United States Patent
Zhu et al.

(10) Patent No.: US 7,378,573 B2
(45) Date of Patent: May 27, 2008

(54) SNOW1: INTERACTS WITH ICE1 AND REGULATES CBF EXPRESSION AND FREEZING TOLERANCE IN ARABIDOPSIS

(75) Inventors: Jian-Kang Zhu, Riverside, CA (US); Manu Agarwal, Riverside, CA (US); Avnish Kapoor, Riverside, CA (US)

(73) Assignee: Arizona Board of Regents on Behalf of University of Arizona, Tuscon, AZ (US)

( * ) Notice: Subject to any disclaimer, the term of this patent is extended or adjusted under 35 U.S.C. 154(b) by 347 days.

(21) Appl. No.: 10/958,411

(22) Filed: Oct. 6, 2004

(65) Prior Publication Data

US 2005/0144671 A1    Jun. 30, 2005

Related U.S. Application Data

(60) Provisional application No. 60/508,316, filed on Oct. 6, 2003.

(51) Int. Cl.
*A01H 5/00* (2006.01)
*C12N 15/82* (2006.01)
*C12N 15/29* (2006.01)

(52) U.S. Cl. .................. 800/298; 435/320.1; 435/419; 435/252.3; 536/23.6; 800/320.3; 800/320.1; 800/314; 800/320; 800/312

(58) Field of Classification Search ............ None
See application file for complete search history.

(56) References Cited

U.S. PATENT DOCUMENTS

2003/0131386 A1    7/2003    Samaha et al.
2005/0144671 A1*   6/2005    Zhu et al.

FOREIGN PATENT DOCUMENTS

WO    WO 0135727    *    5/2001
WO    WO 03/013228 A2    2/2003

OTHER PUBLICATIONS

Reuber L. et al. Database Geneseq Accession No. AAD05765 Jul. 31, 2001.*
Zhizhong Gong, et al., "RNA helicase-like protein as an early regulator of transcription factors for plant chilling and freezing tolerance", Proceedings of the National Academy of Sciences, vol. 99, No. 17, Aug. 20, 2002, pp. 11507-11512.
Yan Guo, et al., "An *Arabidopsis* mutation in translation elongation factor 2 causes superinduction of CBF/DREB1 transcription factor genes but blocks the induction of their downstream targets under low temperatures", Proceedings of the National Academy of Sciences, vol. 99, No. 11, May 28, 2002, pp. 7786-7791.
Jong Cheol Kim, et al., "A novel cold-inducible zinc finger protein from soybean, SCOF-1, enhances cold tolerance in transgenic plants", The Plant Journal, vol. 25, No. 3, 2001, pp. 247-259.
Motoaki Seki, et al., "Monitoring the Expression Pattern of 1300 *Arabidopsis* Genes under Drought and Cold Stresses by Using a Full-Length cDNA Microarray", The Plant Cell, vol. 13, Jan. 2001, pp. 61-72.
Volker Haake, "Transcription Factor CBF4 Is a Regulator of Drought Adaptation in *Arabidopsis*", Plant Physiology, vol. 130, Oct. 2002, pp. 639-648.
Daniel G. Zarka, et al., "Cold Induction of *Arabidopsis* CBF Genes Involves Multiple ICE (Inducer of CBF Expression) Promoter Elements and a Cold-Regulatory Circuit That is Desensitized by Low Temperature", Plant Physiology, vol. 133, Oct. 2003, pp. 910-918.
Viswanathan Chinnusamy, et al., "*ICE1*: a regulator of cold-induced transcriptome and freezing tolerance in *Arabidopsis*". Genes and Development, vol. 17, 2003, pp. 1043-1054.

* cited by examiner

*Primary Examiner*—Cynthia Collins
(74) *Attorney, Agent, or Firm*—Oblon, Spivak, McClelland, Maier & Neustadt, P.C.

(57) ABSTRACT

The present invention relates to a protein (Snow1), mutants thereof, and nucleic acids encoding said protein, that interacts with Ice1 and which activates CBF3 promoter activity thus regulating freezing tolerance in plants.

8 Claims, 8 Drawing Sheets

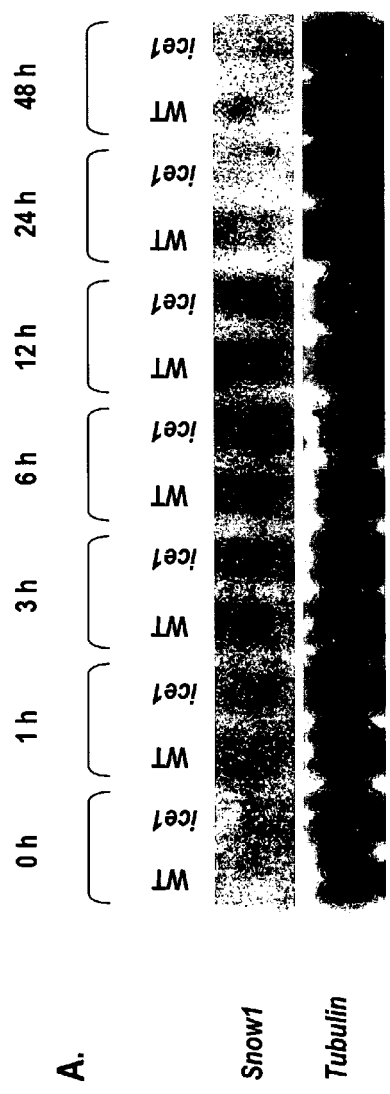
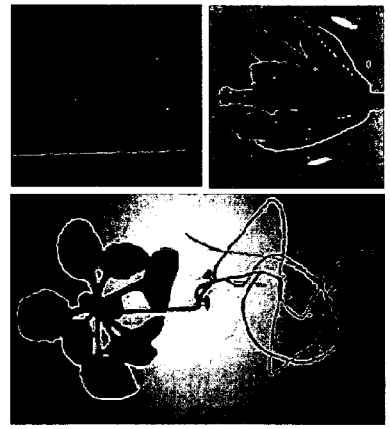
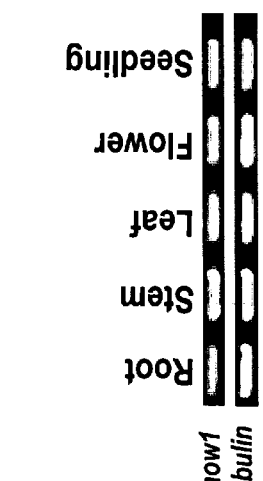
Fig. 1

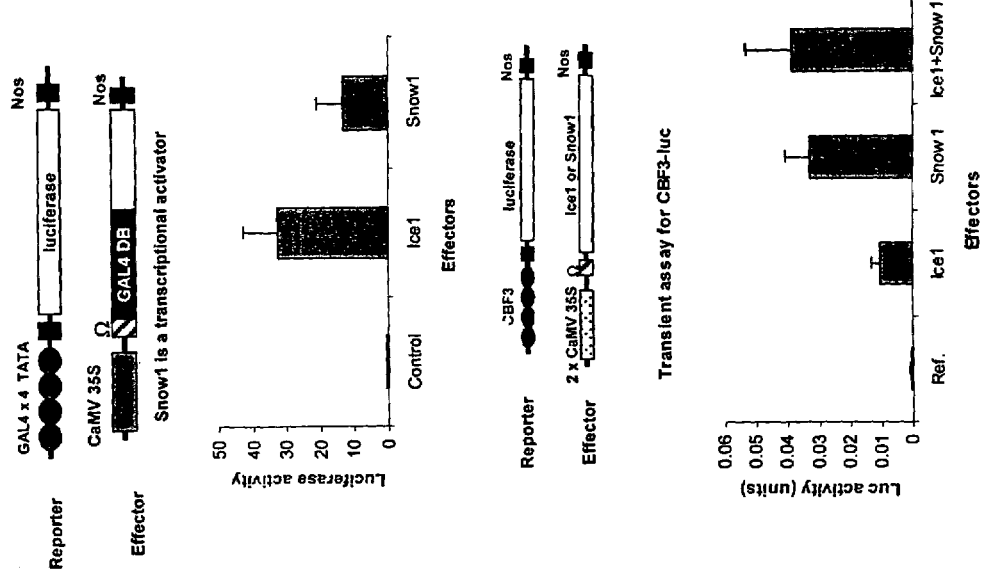
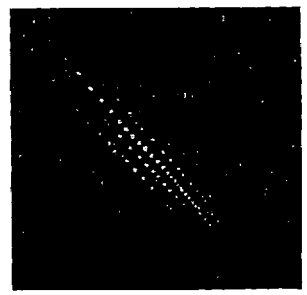
Fig. 4

Fig. 5
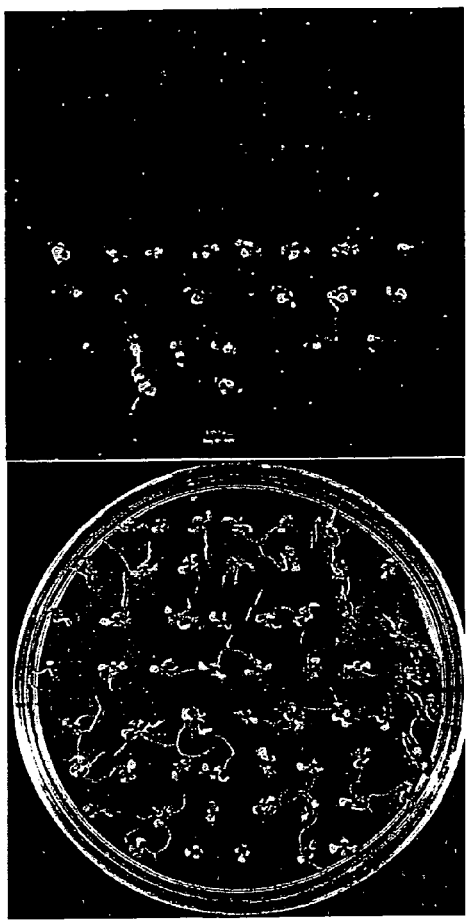
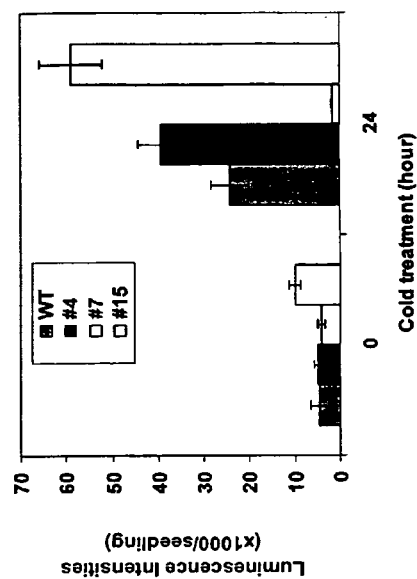
A.
B.

SNOW1: INTERACTS WITH ICE1 AND REGULATES CBF EXPRESSION AND FREEZING TOLERANCE IN *ARABIDOPSIS*

CROSS-REFERENCE TO RELATED APPLICATIONS

The present application claims priority to U.S. 60/508,316, filed on Oct. 6, 2003, which is hereby incorporated by reference in its entirety.

STATEMENT REGARDING FEDERALLY SPONSORED RESEARCH

This work was supported by the National Science Foundation Grant No. MCB0241450. The United States government is entitled to certain rights in the present application.

BACKGROUND OF THE INVENTION

1. Field of the Invention

The present invention relates to a protein, mutants thereof, and nucleic acids encoding said protein, that interacts with Ice1 and which activates CBF3 promoter activity thus regulating freezing tolerance in plants.

2. Discussion of the Background

Adverse low temperature affects the survivability and distribution of almost all living organisms. Plants being sessile have evolved to sense and encounter low temperature stress and their response to adverse low temperature is manifested at physiological, molecular and biochemical levels. Many temperate plants have potential to increase freezing tolerance of these plants after a prior exposure to non freezing temperatures—a process known as cold acclimation (Guy 1990; Hughes and Dunn 1996; Browse and Xin 2001).

At a molecular level a specific set of proteins are induced in response to low temperature that helps plants to sustain adverse low temperature conditions. Moreover, gene expression has been observed to change in response to cold, which is critical for chilling tolerance (Gong et al. 2002; Hsieh et al. 2002) and cold acclimation (Thomashow 1999; Knight et al. 1999; Tahtiharju and Palva 2001). Proteins induced during cold acclimation include enzymes involved in respiration and metabolism of carbohydrates, lipids, phenylpropanoids and antioxidants; molecular chaperones, antifreeze proteins; and many others with presumed function in tolerance to dehydration caused by freezing (Thomashow 1999; Guy 1990; Mohapatra et al 1989). These genes and gene products have been termed CAPs (cold acclimation proteins)/CORs (cold responsive/LTIs (low temperature inducible).

Promoters of many of these genes have DRE/CRT (dehydration responsive element/C-repeat), a cis element necessary and sufficient for gene transcription under cold stress (Yamaguchi-Shinozaki and Shinozaki 1994; Stockinger et al 1997). A small group of homologous transcription factors (CBF/DREB) bind to this sequence and induce cold-regulated gene expression (Stockinger et al 1997; Liu et al 1998). Recently the present inventors have identified an upstream factor that binds to the Myc like sequences of the CBF3 promoter and is a critical determinant of CBF3 expression and freezing tolerance in *Arabidopsis* (Chinnusamy et al 2003). Apart from the Myc like sequences in CBF3 promoter there are many putative Myb like sequences (Shinwari et al 1998). MYC-related bHLH transcription factors require MYB co-transcription factors and/or WD-repeat containing factors for transcriptional activation of target genes (Spelt et al. 2000; Walker et al. 1999).

Chinnusamy et al (2003) proposed that possibly a Myb like transcription factor interacts with Ice1 and causes cold-induced expression of CBF genes. Importantly, microarray analysis show more levels of Snow1 (previously referred to as AtMyb15 in U.S. 60/508,316 to which the present application claims priority and which is incorporated herein by reference in its entirety) transcript in ice1 mutant when compared to wild type plants under conditions of cold stress (Chinnusamy et al 2003). This indicates that in absence of Ice1 function, more levels of Snow1 may be produced to compensate the loss of function of Ice1.

Since environmental factors, such as cold, limits the geographical distribution and growing season of many plant species, and often adversely affects crop quality and productivity, there remains an ongoing critical need to increase cold tolerance and/or cold acclimation in plants, particularly those plants that are advantageously useful as agricultural crops.

SUMMARY OF THE INVENTION

It is an object of the present invention to provide methods and compositions for increasing cold tolerance and/or cold acclimation (hereinafter referred to simply as cold acclimation) in plants.

It is another object of the present invention to provide transgenic plants and plant cells, which have increased acclimation.

The objects of the present invention, and others, may be accomplished with a method of increasing cold acclimation in a plant, comprising overexpressing Snow1 in the plant.

The objects of the present invention may also be accomplished with a method of increasing cold acclimation in a plant cell, comprising overexpressing Snow1 in the plant cell.

The objects of the present invention may also be accomplished with a plant or a plant cell transformed with a nucleic acid that encodes Snow1.

Thus, the present invention also provides a method of producing such a plant or plant cell, by transforming a plant or plant cell with the nucleic acid that encodes Snow1.

The present invention also provides an isolated and purified Snow1 having the amino acid sequence of SEQ ID NO: 2.

The present invention also provides a method of producing the Snow1 described above, comprising culturing host cells that have been transformed with a nucleic acid encoding Snow1 under conditions in which Snow1 is expressed, and isolating Snow1.

In another embodiment, the present invention provides an isolated and purified enzyme having Snow1 transcriptional activator activity, wherein the amino acid sequence of the enzyme has a homology of from 70% to less than 100% to SEQ ID NO: 2.

The present invention also provides a method of producing the enzyme described above, comprising culturing host cells that have been transformed with a nucleic acid encoding the enzyme under conditions in which the enzyme is expressed, and isolating the enzyme.

The present invention also provides a method of increasing cold acclimation in a plant, comprising overexpressing a Snow1 transcriptional activator in the plant.

The present invention also provides a method of increasing cold acclimation in a plant by increasing the expression of one or more additional transcription factors selected from the group consisting of a CBF transcription factor and a DREB1 transcription factor and/or by increasing expression of one or more cold-responsive genes.

The present invention further provides the aforementioned cells and methods wherein Ice1 is co-expressed with Snow1 to complement the obtained increase in cold acclimation.

Herein the present inventors assessed the ability of Snow1 to alter the expression of CBF3. Both microarray and northern analysis confirmed increased levels of Snow1 transcript in ice1 phenotype cells. Snow1 is constitutive, ubiquitous and nuclear localized. Snow1 can physically interact with Ice1 as determined by yeast 2-hybrid and protein pull-down assays. Snow1 protein binds to Myb-like recognition sequences in CBF3 promoter and its transient expression increases the luciferase activity of CBF3 driven luciferase gene thus indicating its role in cold acclimation and cold tolerance. Transgenic plants (CBF3-luc) overexpressing Snow1 show enhanced luminescence under conditions of cold stress. These results suggest that Snow1 is an activator of the CBF3 expression.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 1: Snow1 is constitutively and ubiquitously expressed in plants. (A). Snow1 transcript in WT (CBF3-luc) and ice1 plants under normal and cold stressed conditions. The tubulin gene was used as a loading control (B). Snow1 transcript in different organs of *Arabidopsis* plants. 2 µg of total RNA was reverse transcribed followed by PCR using gene specific primers for Snow1 and Tubulin as a control. (C). Histochemical localization of Gus protein in different organs of *Arabidopsis* seedlinds.

FIG. 4: Snow1 is a nuclear localized transcriptional activator and its overexpression increases CBF3 expression. (A). Localization of GFP-Snow1 protein in nucleus. The panel shows confocal images in root cells of GFP-Snow1 transgenic plants. (B). Relative luciferase activities after transfection with CBF3-LUC and 35S-Snow1 and/or 35S-Ice1. To normalize values obtained after each transfection, a gene for luciferase from *Renilla* was used as an internal control. Luciferase activity is expressed in arbitrary units relative to the activity of *Renilla* luciferase (as described in Ohta et al. 2001).

FIG. 5: A. Images of seedlings and luminescence of the wild type and the Snow1 over expression line (# 7). Images were after cold 12 h treatment. B. Quantitation of luminescence intensities from the wild type and the Snow1 over expression line (# 4, 7 & 15) during cold stress.

DETAILED DESCRIPTION OF THE INVENTION

Figure 2:
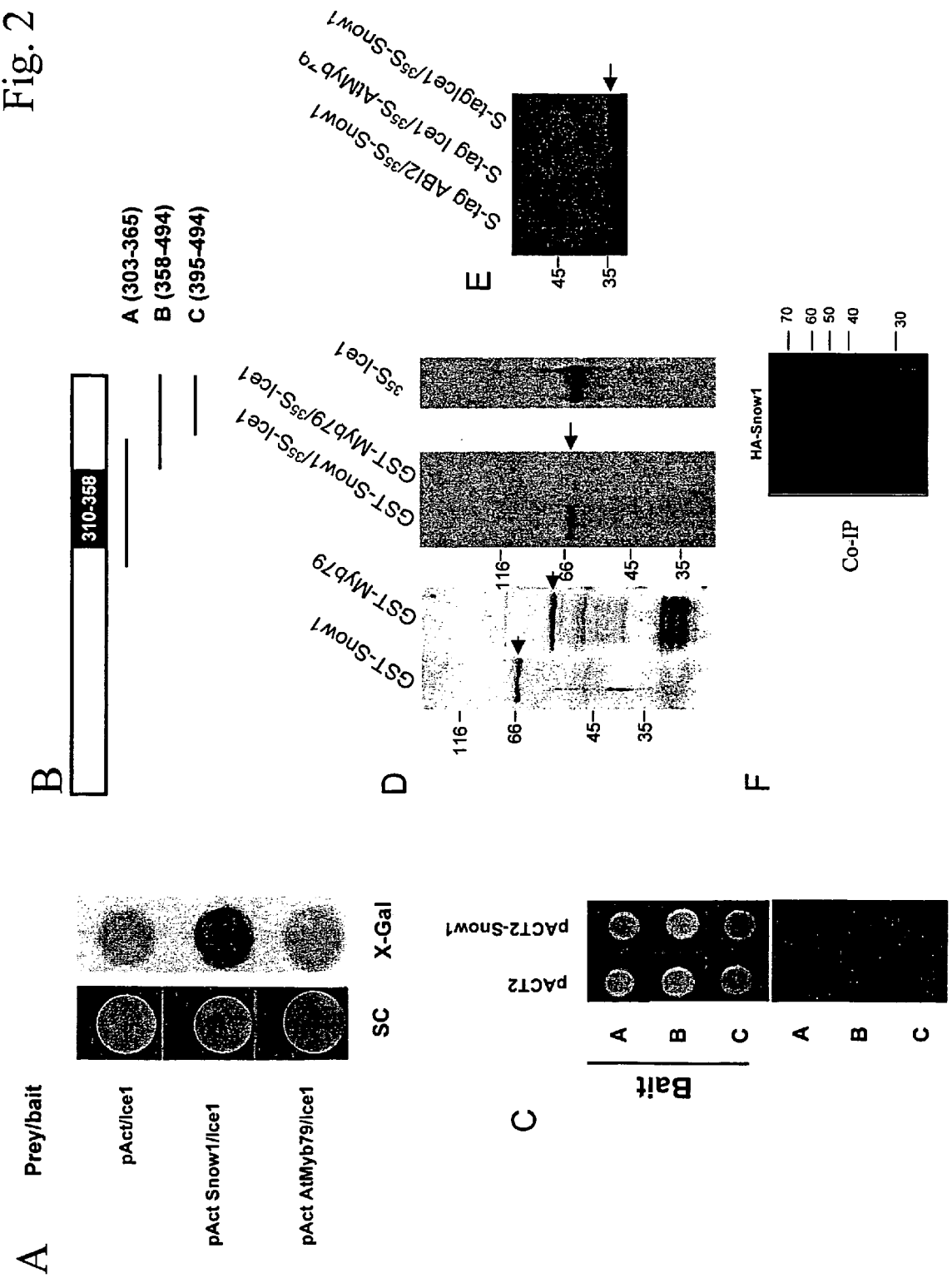
FIG. 2: Snow1 specifically interacts with Ice1. (A). Different prey and bait combinations used for studying 2-hybrid interactions are indicated. (B). Different regions of Ice1 used as bait to fine map its interacting domain with Snow1. These regions are depicted as A through F. The boxed region in the line diagram represents the bHLH region of Ice1 protein. (C). Interaction of the depicted regions of Ice1 with Snow1 bait. (D). In-vitro pull down using GST-tagged proteins. The combinations used are indicated at the top and the molecular weight markers are indicated on the left of the panel. Commassie stained gel of the GST-tagged purified proteins is shown in the left panel and the autoradiogram is shown in the right panel. (E). In-vitro pull down using S-tagged proteins. The combinations used are indicated at the top and the molecular weight markers are indicated on the left of the panel. (F) In vivo interaction of Ice1 with Snow1. *Arabidopsis* protoplasts were transformed with Myc-Ice1 and HA-Snow1. Myc tagged Ice1 was immunoprecipitated with anti c-Myc antibodies. The proteins were resolved on SDS-PAGE and transferred to Nitrocellulose membrane and the membrane was probed with anti HA antibodies. Protein molecular weight markers are indicated on the right of the panel.

Unless specifically defined, all technical and scientific terms used herein have the same meaning as commonly understood by a skilled artisan in enzymology, biochemistry, cellular biology, molecular biology, plant biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

Cold stress induces a number of genes that are regulated in turn by cold-induced expression of a battery of transcription factors. The CBF class of transcription factors includes some of the major determinants of cold response in crop plants. Recently, the present inventors reported that the expression of CBF genes is regulated by ice1, another upstream transcription factor. Ice1 binds to MYC-like recognition sequences in the CBF3 promoter. Apart from the MYC-like recognition sequences, the CBF3 promoter also has MYB-like sequences. Chinnusammy et al (2003) proposed existence of another transcription factor that binds to MYB-like recognition sequences and regulates CBF3 expression. The present inventors scanned the microarray data (Chinnusammy et al 2003) and found one MYB transcription factor that shows high transcript levels in ice1 mutant under cold stress. Considering that loss of function of one gene can be compensated by increased expression of another gene, the present inventors investigated the role of Snow1 in regulating CBF3 expression.

Northern analysis reveals that Snow1 is slightly induced by cold stress indicating that Snow1 has potentially same role in encountering cold stress. Consistent with the micro array data, Northern analysis shows the presence of increased levels of Snow1 transcript in ice1 mutant under conditions of low temperature stress. Enhanced expression of Snow1 may be to compensate the loss of function of Ice1. Snow1 is expressed constitutively in all tissues and is nuclear-localized. EMSA shows that Snow1 binds to the CBF3 promoter and specifically requires myb-like recognition sequences of CBF3 promoter. Binding of Snow1 to CBF3 promoter indicates that it regulates the expression of CBF3 promoter.

Snow1 physically interacts with ice1. Yeast two hybrid analysis shows that Snow1 interacts with C-terminal portions (a.a. 266-499) of Ice1. Additionally the specific interaction of Snow1 with Ice1 has been narrowed down to 358-494 a.a. of Ice1. Furthermore both Ice1 and Snow1 are able to interact as determined by protein pull down assays. The interaction was specific as a distant MYB transcription factor (Myb79) was not able to interact with Ice1. Combinatorial interactions between transcription factors have been shown to be important for the regulation of down stream genes (Walker et al 1999, Spelt et al 2000, Grotewold et al 2000). Results of transient assay show that overexpression of Snow1 increases the expression of CBF3 promoter driven luciferase. There was a marginal increase in luciferase activity when Ice1 was co-bombarded with Snow1. This indicates that both ice1 and Snow1 act independently to activate CBF3 expression in vivo and their interaction does not super enhance CBF3 expression. It is possible that induction of CBF3 expression by these two transcription factors is distributed with respect to the inception of cold stress duration. Transgenic plants (CBF3-luc background) constitutively expressing Snow1 under the control of CaMV35S promoter shows enhanced luminescence under cold stress when compared to wild type plants. All these results show that Snow1 is a transcriptional activator of CBF3 expression.

Accordingly, the present invention is embodied by the description provided herein and further explained and exemplified below.

The term "plant" includes whole plants, plant organs (e.g., leaves, stems, roots, etc.), seeds and plant cells and progeny of same. The class of plants, which can be used in the methods of the invention, is generally as broad as the class of higher plants amenable to transformation techniques, including both monocotyledonous and dicotyledonous plants. Preferred plants include rice, corn, wheat, cotton, peanut, and soybean.

The term "plant" includes whole plants, plant organs (e.g., leaves, stems, roots, etc.), seeds and plant cells and progeny of same. The class of plants, which can be used in the methods of the invention, is generally as broad as the class of higher plants amenable to transformation techniques, including both monocotyledonous and dicotyledonous plants. Preferred plants include rice, corn, wheat, cotton, peanut, and soybean.

Thus, in one embodiment of the present invention, cold acclimation can be enhanced or increased by increasing the amount of protein available in the plant, preferably by the enhancement of the snow1 gene in the plant.

Thus, one embodiment of the present invention is plant cells carrying the polynucleotides of the present invention, and preferably transgenic plants carrying the isolated polynucleotides of the present invention.

As used herein, the term "enhancement" means increasing the intracellular activity of one or more enzymes in a plant cell and/or plant, which are encoded by the corresponding DNA. Enhancement can be achieved with the aid of various manipulations of the bacterial cell. In order to achieve enhancement, particularly over-expression, the number of copies of the corresponding gene can be increased, a strong promoter can be used, or the promoter and regulation region or the ribosome binding site which is situated upstream of the structural gene can be mutated. Expression cassettes which are incorporated upstream of the structural gene may act in the same manner. In addition, it is possible to increase expression by employing inducible promoters. A gene can also be used which encodes a corresponding enzyme with a high activity. Expression can also be improved by measures for extending the life of the mRNA. Furthermore, preventing the degradation of the enzyme increases enzyme activity as a whole. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995).

An "expression cassette" as used herein includes a promoter, which is functional in a plant cell, operably linked to a nucleic acid encoding an Snow1 protein of SEQ ID NO: 2 (e.g., a polynucleotide having the sequence of SEQ ID NO: 1), wherein enhanced expression of the protein in a plant cell imparts increased cold acclimation to said plant cell. In a preferred embodiment of the present invention the promoter is selected from the group consisting of a viral coat protein promoter, a tissue-specific promoter, a monocot promoter, a ubiquitin promoter, a stress inducible promoter, a CaMV 35S promoter, a CaMV 19S promoter, an actin promoter, a cab promoter, a sucrose synthase promoter, a tubulin promoter, a napin R gene complex promoter, a tomato E8 promoter, a patatin promoter, a mannopine synthase promoter, a soybean seed protein glycinin promoter, a soybean vegetative storage protein promoter, a bacteriophage SP6 promoter, a bacteriophage T3 promoter, a bacteriophage T7 promoter, a Ptac promoter, a root-cell promoter, an ABA-inducible promoter and a turgor-inducible promoter. Further, in another example of the expression cassette of the present invention is as described above for Snow1, but rather it contains a nucleic acid encoding an Ice1 protein of SEQ ID NO: 4 (e.g., a polynucleotide having the sequence of SEQ ID NO: 3), wherein enhanced expression of the protein in a plant cell imparts increased cold acclimation to said plant cell. In yet another embodiment, the expression cassette may contain both polynucleotides encoding Snow1 and Ice1 (these polynucleotides and the variants thereof are described below), either under the control of the same promoter or a selectively inducible promoter, on the same (or different) plasmid or vector. As used herein the term "selectively inducible promoter" means that when two or more promoters are present on the same plasmid or vector, or when these promoters are present on a different plasmid or vector but the plasmids or vectors are contained in the same host cell, plant cell, or transgenic plant, these promoters are compatible with the host (stably maintained by the host cell, plant cell, or transgenic plant) and may be individually activated or transcription enhanced (e.g., by addition of IPTG in the case of one promoter and by an increase in temperature in another).

A gene can also be used which encodes a corresponding or variant enzyme (e.g., Snow1 and/or Ice1) with a high activity. Preferably the corresponding enzyme has a greater activity than the native form of the enzyme, more preferably at least in the range of 5, 10, 25% or 50% more activity, most preferably more than twice the activity of the native enzyme.

In the context of the present application, a polynucleotide sequence is "homologous" with the sequence according to the invention if at least 70%, preferably at least 80%, more preferably at least 90%, most preferably at least 95% of its base composition and base sequence corresponds to the sequence according to the invention. According to the invention, a "homologous protein" is to be understood to comprise proteins which contain an amino acid sequence at least 70%, preferably at least 80%, more preferably at least 90%, most preferably at least 95% of which, corresponds to the amino acid sequence according to the present invention or which is encoded by the aforementioned polynucleotide sequence, wherein corresponds is to be understood to mean that the corresponding amino acids are either identical or are mutually homologous amino acids. As set forth herein, the sequences of the present invention correspond to SEQ ID NO: 1 (polynucleotide sequence: snow1), SEQ ID NO: 2 (amino acid sequence: Snow1), SEQ ID NO: 3 (polynucleotide sequence: ice1), and SEQ ID NO: 4 (amino acid sequence: Ice1). The expression "homologous amino acids" denotes those that have corresponding properties, particularly with regard to their charge, hydrophobic character, steric properties, etc. Thus, the protein may be from 70% up to less than 100% homologous to SEQ ID NO: 2 or SEQ ID NO:4.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The present invention also relates to polynucleotides that contain the complete gene with the polynucleotide sequence corresponding to SEQ ID NO: 1, or fragments thereof, and which can be obtained by screening by means of the hybridization of a corresponding gene bank with a probe which contains the sequence of said polynucleotide corresponding to SEQ ID NO: 1, or fragments thereof, and isolation of said DNA sequence.

Polynucleotide sequences according to the invention are suitable as hybridization probes for RNA, cDNA and DNA, in order to isolate those cDNAs or genes which exhibit a high degree of similarity to the sequence of the snow1 gene, in particular the snow1 gene of SEQ ID NO: 1.

Polynucleotide sequences according to the invention are also suitable as primers for polymerase chain reaction (PCR) for the production of DNA which encodes an enzyme having Snow1 transcriptional activator activity.

Oligonucleotides such as these, which serve as probes or primers, can contain more than 30, preferably up to 30, more preferably up to 20, most preferably at least 15 successive nucleotides. Oligonucleotides with a length of at least 40 or 50 nucleotides are also suitable.

The term "isolated" means separated from its natural environment. It is to be understood that the "isolated" polynucleotides and polypeptides of the present invention may further be substantially pure or pure (i.e., the polynucleotides and polypeptides have been purified). As used herein, the term "substantially pure" means that the polynucleotides and polypeptides have been isolated from its natural environment to an extent such that only minor impurities remain (e.g., the resultant polynucleotides and polypeptides are at least 70%, preferably at least 80%, more preferably at least 90%, most preferably at least 95% pure). As used herein, the term "pure" means that the polynucleotides and polypeptides are free from contaminants (i.e., are 100% pure).

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins, which contain two or more amino acids which are bound via peptide bonds.

The polypeptides according to invention include polypeptides corresponding to SEQ ID NO: 2, particularly those with the biological activity of a Snow1 transcriptional activator, and also includes those, at least 70% of which, preferably at least 80% of which, more preferably at least 90% of which, most preferably at least 95% of which, are homologous with the polypeptide corresponding to SEQ ID NO: 2 and which have the cited activity. Thus, the polypeptides may have a homology of from 70% up to 100% with respect to SEQ ID NO:2.

The invention also relates to coding DNA sequences, which result from SEQ ID NO: 1 by degeneration of the genetic code. In the same manner, the invention further relates to DNA sequences which hybridize with SEQ ID NO: 1 or with parts of SEQ ID NO: 1. Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilize said function.

In the same manner, the present invention also relates to DNA sequences which hybridize with SEQ ID NO: 1 or with parts of SEQ ID NO: 1. The present invention also relates to DNA sequences that are produced by polymerase chain reaction (PCR) using oligonucleotide primers which result from SEQ ID NO: 1. Oligonucleotides of this type typically have a length of at least 15 nucleotides as defined above.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the Tm can be approximated from the equation of Meinkoth and Wahl, Anal. Biochem., 138:267-284 (1984): $Tm=81.5° C.+16.6 (\log M)+0.41 (\% GC)-0.61 (\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Thus, with the foregoing information, the skilled artisan can identify and isolated polynucleotides that are substantially similar to the present polynucleotides. In so isolating such a polynucleotide, the polynucleotide can be used as the present polynucleotide in, for example, increasing cold acclimation of a plant.

One embodiment of the present invention is methods of screening for polynucleotides that have substantial homology to the polynucleotides of the present invention, preferably those polynucleotides encoding a protein having Snow1 transcriptional activator activity.

The polynucleotide sequences of the present invention can be carried on one or more suitable plasmids or vectors, as known in the art for plants or the like. As stated above, it is also within the scope of the present invention to have the polynucleotide sequences (SEQ ID NO: 1 and SEQ ID NO: 3) on the same or different plasmids or vectors. In an embodiment of the present invention, these polynucleotides may be operably linked to a single promoter, different promoters of the same type, or selectively inducible promoters, on the same (or different) plasmid or vector.

In one embodiment, it may be advantageous for propagating the polynucleotide to carry it in a bacterial or fungal strain with the appropriate vector suitable for the cell type. Common methods of propagating polynucleotides and producing proteins in these cell types are known in the art and are described, for example, in Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989).

In another preferred embodiment the polynucleotide comprises SEQ ID NO: 1, polynucleotides which are complimentary to SEQ ID NO: 1, polynucleotides which are at least 70%, 80%, 90%, or 95% identical to SEQ ID NO: 1; or those sequence which hybridize under stringent conditions to SEQ ID NO: 1, the stringent conditions comprise washing in 5×SSC at a temperature from 50 to 68° C. Thus, the polynucleotide may be from 70% up to less than 100% identical to SEQ ID NO: 1.

In an embodiment of the present invention, the polynucleotides of the present invention (i.e., SEQ ID NO: 1, a variant thereof, a polynucleotide encoding SEQ ID NO: 2, or a variant thereof as described above) are contained in a plasmid or vector either in the absence of presence of a polynucleotide relating to Ice1 (i.e., SEQ ID NO: 3, a variant thereof, a polynucleotide encoding SEQ ID NO: 4, or a variant thereof as described above).

In another embodiment of the present invention, the plasmid(s) or vector(s) of the present invention are contained in a host cell, a plant cell, or a transgenic plant. Preferably, the plant is *Arabidopsis thaliania* or selected from the group consisting of wheat, corn, peanut cotton, oat, and soybean plant. In a preferred embodiment, the polynucleotides (encoding Snow1 and/or Ice1 as defined above) are operably linked to a promoter, preferably an inducible promoter. As described hereinabove, the polynucleotides may be operably linked to a single promoter, different promoters of the same type, or selectively inducible promoters, on the same (or different) plasmid or vector.

In another preferred embodiment the present invention provides a process for screening for polynucleotides which encode a protein having Snow1 transcriptional activator activity comprising hybridizing the polynucleotide of the invention to the polynucleotide to be screened; expressing the polynucleotide to produce a protein; and detecting the presence or absence of Snow1 transcriptional activator activity in the protein.

In another preferred embodiment, the present invention provides a method for detecting a nucleic acid with at least 70% homology to nucleotide SEQ ID NO: 1, sequences which are complimentary to SEQ ID NO: 1 and/or which encode a protein having the amino acid sequence in SEQ ID NO: 2 comprising contacting a nucleic acid sample with a probe or primer comprising at least 15 consecutive nucleotides of the nucleotide sequence of SEQ ID NO: 1, or at least 15 consecutive nucleotides of the complement thereof.

In another preferred embodiment, the present invention provides a method for producing a nucleic acid with at least 70% homology to the polynucleotides of the present invention comprising contacting a nucleic acid sample with a primer comprising at least 15 consecutive nucleotides of the nucleotide sequence of SEQ ID NO: 1, or at least 15 consecutive nucleotides of the complement thereof.

In another preferred embodiment, the present invention provides a method for making Snow1 protein, comprising culturing the host cell carrying the polynucleotides of the invention for a time and under conditions suitable for expression of Snow1, and collecting the Snow1.

In another preferred embodiment, the present invention provides a method of making a transgenic plant comprising introducing the polynucleotides of the invention into the plant.

In another preferred embodiment, the present invention provides method of increasing cold acclimation of a plant in need thereof, comprising introducing the polynucleotides (inclusive of the polynucleotides defined herein for snow1 alone or in the presence of the polynucleotides defined herein for ice1) of the invention into said plant.

Methods, vectors, and compositions for transforming plants and plant cells in accordance with the invention are well-known to those skilled in the art, and are not particularly limited. For a descriptive example see Karimi et al., TRENDS in Plant Science, Vol. 7, NO: 5, May 2002, pp. 193-195, incorporated herein by reference.

In another preferred embodiment, the present invention provides an isolated polypeptide comprising the amino acid sequence in SEQ ID NO: 2 or those proteins that are at least 70%, preferably 80%, more preferably 90% and most preferably 95% homology to SEQ ID NO: 2, where the polypeptides have ICE1 transcriptional activator activity. Thus, the enzyme has a homology of from 70% to less than 100% homology to SEQ ID NO: 2.

In another embodiment, the present invention also provides a method of increasing cold acclimation in a plant, comprising overexpressing an Snow1 transcriptional activator in the plant. In this embodiment, Snow1 may further be co-expressed with Ice1.

The present invention also provides, in another embodiment a method of increasing cold acclimation in a plant by increasing the expression of one or more additional transcription factors selected from the group consisting of a CBF transcription factor and a DREB1 transcription factor and/or by increasing expression of one or more cold-responsive genes.

In the context of the present invention the term "cold responsive genes" include genes that encode a protein selected from the group consisting of an enzyme involved in respiration of carbohydrates, an enzyme involved in metabolism of carbohydrates, an enzyme involved in respiration of lipids, an enzyme involved in metabolism of lipids, an enzyme involved in respiration of phenylpropanoids, an enzyme involved in metabolism of phenylpropanoids, an enzyme involved in respiration of antioxidants, an enzyme involved in metabolism of antioxidants, a molecular chaperone, an antifreeze protein, and a protein involved in tolerance to the dehydration caused by freezing.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Materials and Methods

Gene expression analysis: For RNA analysis, ten-day old seedlings of wild-type and ice1 (phenotype) plants grown on separate halves of the same MS plate were used. Total RNA extracted from control and stressed plants were analyzed by RNA blotting as described by Liu and Zhu (1997). RNA from the transgenic plants overexpressing Snow1 was extracted as described. The RNA was transferred to a nylon membrane and the membrane was either probed with full-length snow1 cDNA or CBF3. β-tubulin gene was amplified by PCR as described (Chinnusamy et al 2003) and was used as a loading control. For expression analysis in various tissues, RNA was extracted from root, leaf, stem, flower and silique and was subsequently analyzed by RNA blotting using full-length snow1 cDNA as a probe. The open reading frame of ICE1 (SEQ ID NO: 3) was determined by sequencing cDNAs obtained by RT-PCR (see U.S. application Ser. No. 10/425,913, the entire contents of which are incorporated by reference).

Yeast two hybrid interaction studies: Full-length Snow1 was amplified using primers 5' GATGGGAAGAGCTC-CATGCTG 3' (SEQ ID NO: 5) and 5' CCGCTC-GAGCTAGCCAATACATCGAACCAG 3' (SEQ ID NO: 6) and was cloned in the SmaI and XhoI sites of the pACT2 vector (prey vector). C-terminal region (corresponding to 266-494 amino acids) of Ice1 was amplified from pMal-Ice1 DNA (Ice1 cloned in MBP fusion vector) as template using 5' TGAGACTGGGATTGAGGTTTCTG 3' (SEQ ID NO: 7) and 5'CAAGCTTGCCTGCAGGTCGAC 3' (SEQ ID NO:

8) primers and was cloned in the SmaI and SalI sites of pAS2 vector (bait vector). For mapping of the interacting domain deletions of C-terminal portion of Ice1 were PCR-amplified using gene specific primers and were cloned in NcoI and BamHI sites of pAS2 vector. Prey and different bait plasmids were co-transformed in Y190 strain of yeast and colonies were selected on SC-Trp,Leu medium. Resultant colonies were assayed for β-Gal activity.

Expression and Purification of Fusion Protein in *E. Coli*: Full-length snow1 cDNA (cloned in pGEMT-easy) was amplified using gene specific primer CG GGATCCATGGGAAGAGCTCCATGCTGTG (SEQ ID NO: 9) and SP6 primer. The amplicon was cloned in BamH I and Sal I sites of pMAL vector (NEB) or pGEX 4T-1 vector (Pharmacia, USA). Full-length AtMyb79 cDNA was amplified using CG GGATCCGAATGGTGGAAGAAGTTTGGAGAAA (SEQ ID NO: 10) and CCG CTCGAGTTAACAAAATGGAATCACCAAGTT (SEQ ID NO: 11) and was cloned in BamH I and Xho I sites of pGex 4T-1 vector (Pharmacia). The MBP-Snow1 fusion protein was purified as per the instructions provided by the manufacturers. GST-fused Snow1, GST-fused Atmyb79 (a distant MYB transcription factor) constructs were transformed into *E. coli* BL21 (codon plus) cells (Stratagene). Single colonies were grown overnight at 37° C., transferred to fresh 20× volume of Luria-Bertani media, and further cultured for 1 hour. Recombinant protein expression was induced by 1 mM isopropyl beta-D-thiogalactopyranoside for 4 h at 37° C. The cells were harvested by centrifugation (5,000×g, 10 min, 4° C.), and the pellets were resuspended in pre-chilled lysis buffer (10 mM Tris pH8.0, 150 mM NaCl, 1 mM EDTA and 100 µg/ml lysozyme), incubated on ice for 15 min. Dithiothreitol (50 mM), phenylmethanesulfonyl fluoride (1 mM) and N-lauroyl sarcosine (1%) were added before 1 min-sonication. The sonicate was clarified by centrifugation at 30,000×g for 15 min 4° C. Triton X-100 (1.5%) was added in the supernatant and vortexed. Prepared glutathione-agarose beads (Sigma). The beads were washed six times with pre-chilled PBS. GST-fused proteins were eluted with 100 mM glutathione (Sigma), 50 mM Tris, pH 8.8. His-tagged ICE1 was eluted with pre-chilled PBS containing 1 M imidazole.

Figure 3:
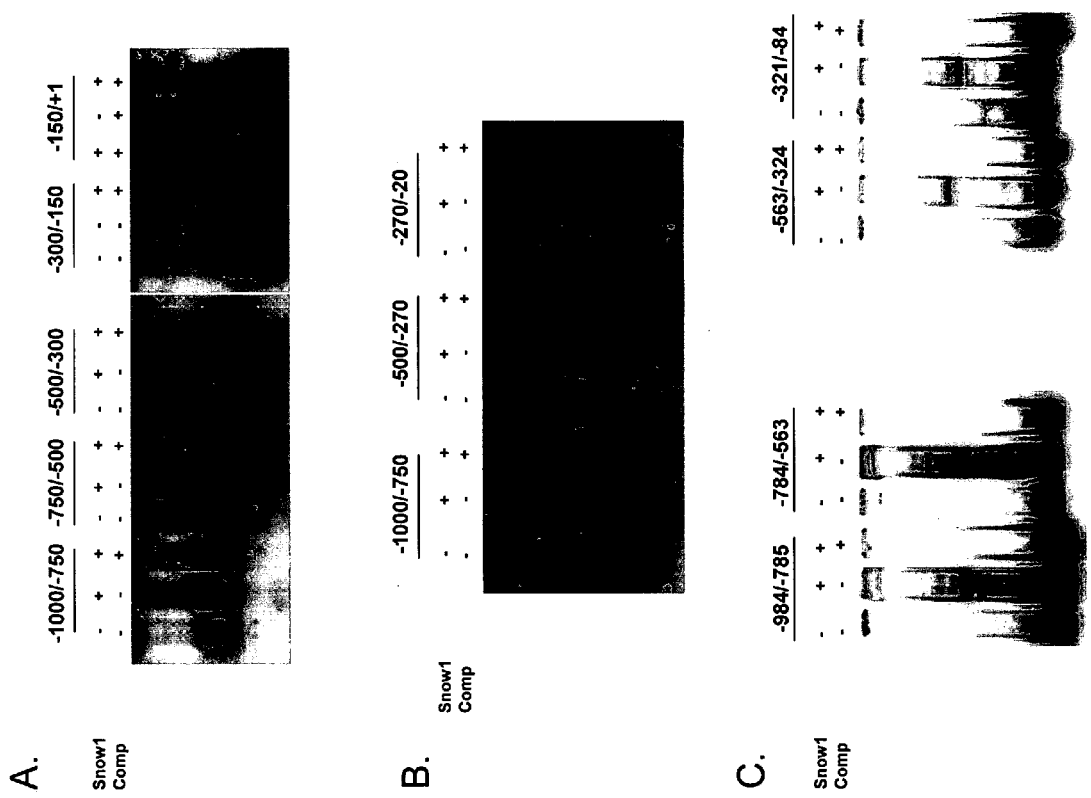
FIG. 3: Snow1 protein binds to different portions of CBF promoters. (A). Interaction between Snow1 protein and portions of CBF1 promoter. (B). Interaction between Snow1 protein and portions of CBF2 promoter. (C). Interaction between Snow1 protein and portions of CBF3 promoter. Different fragments used are indicated at the top of each panel.
Figure 6:
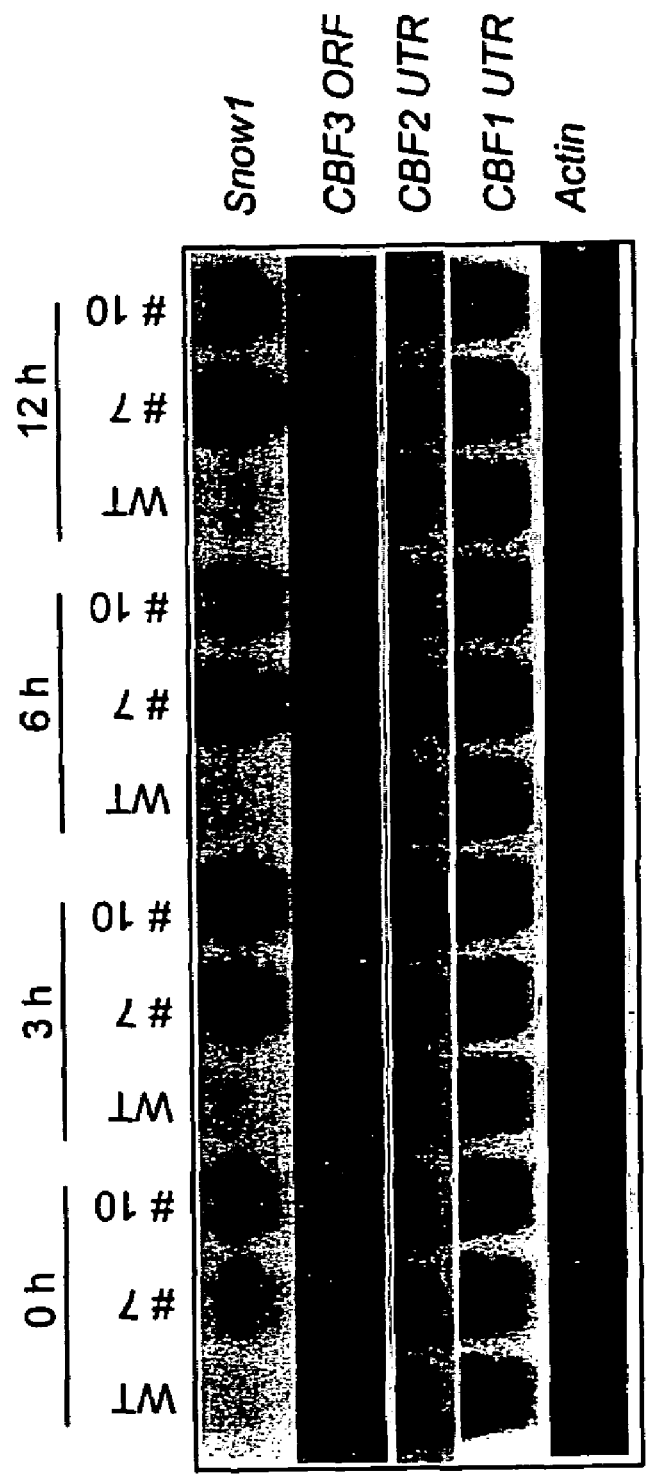
FIG. 6: Steady state levels of Snow1 abd CBF3 transcripts in Snow1 overexpression lines # 7 and # 10. The lines used are indicated on the right and the cold stress treatment (00 C) is indicated on the top. Actin was used as endogenous control.
Figure 7:
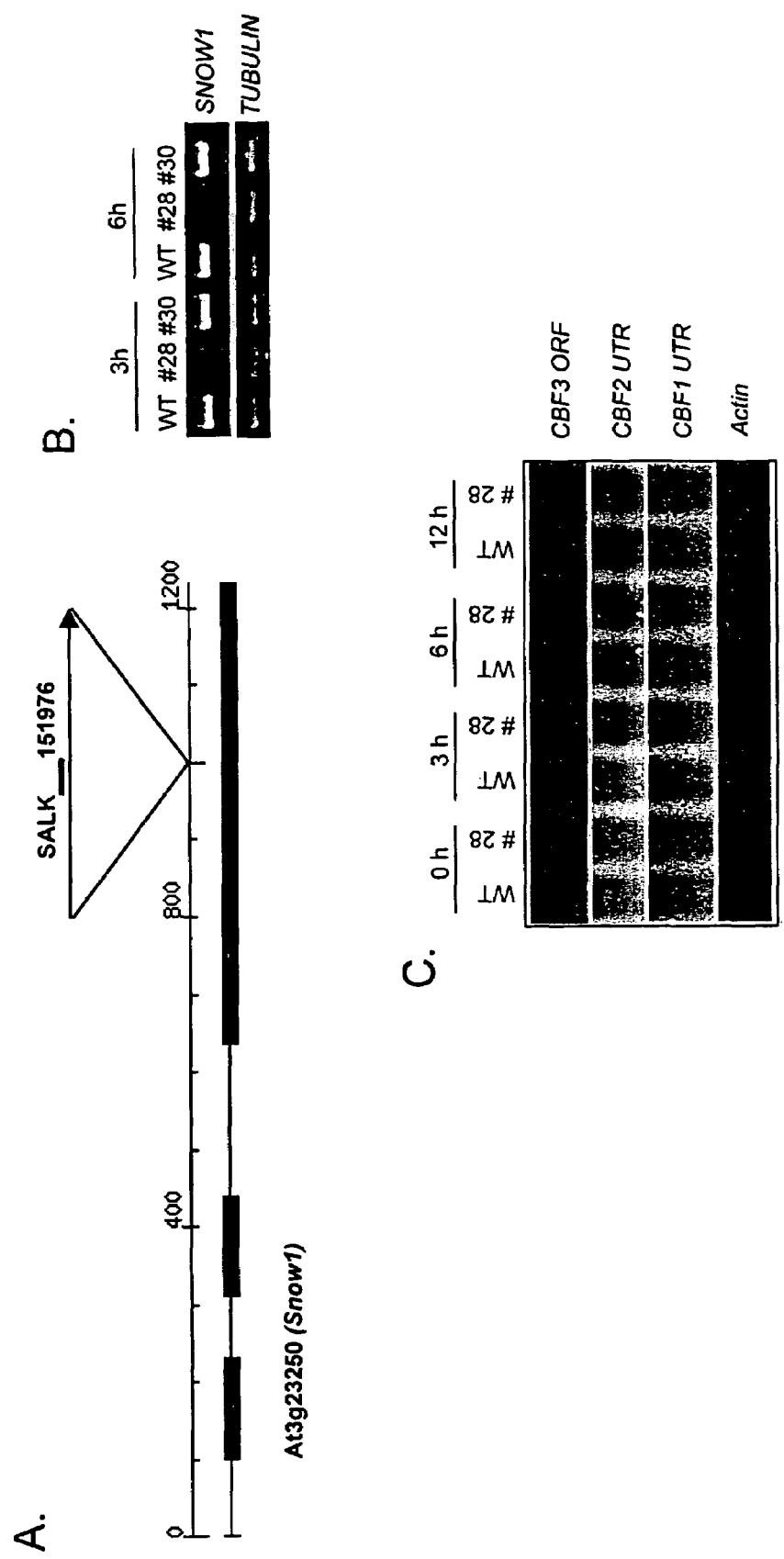
FIG. 7: Analysis of Snow1 T-DNA line. (A) Representation of the T-DNA integration in the Snow1 gene. (B) Gene knock out was confirmed by RT-PCR of the homozygous (# 28) and a heterozygous (# 30) T-DNA lines. WT—wild type, tubulin was used as an internal control. (C) Levels of CBF genes in wild type (WT) and homozygous T-DNA line (# 28) under control and cold stress conditions.
Figure 8:
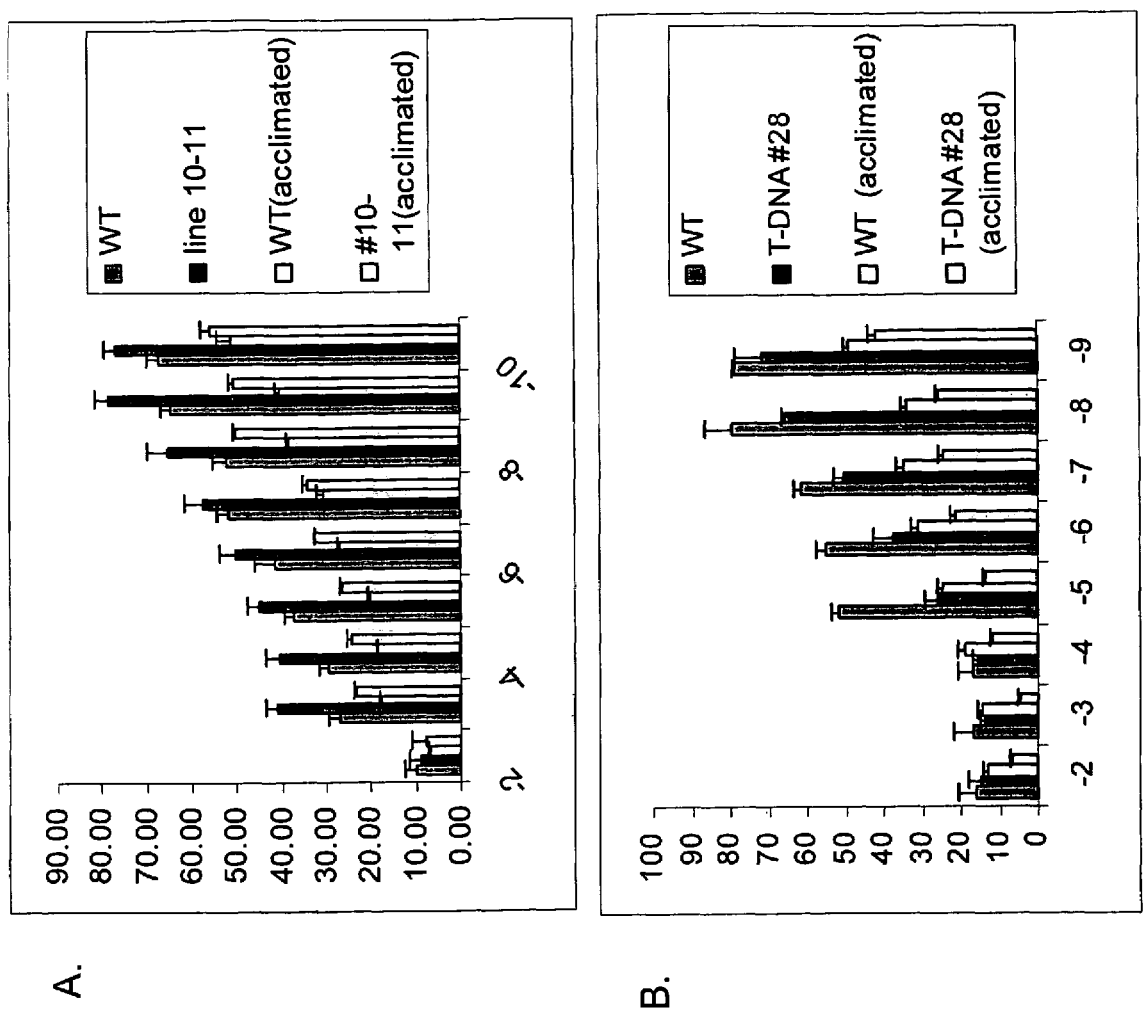
FIG. 8: Ion-leakage of the homozygous overexpression and T-DNA lines of Snow1. Conductivity was measured after cold stress of leaves from acclimated as well as non-acclimated plants. (A) Conductivity of Snow1 overexpression line. (B) Conductivity of Snow1 T-DNA line.

DNA binding: For binding with CBF promoters, different fragments were PCR amplified from the CBF promoters (for details of the regions used see FIG. 3) using KOD polymerase (Novagen). Amplified fragments were eluted from agaorse gel using Qiaquick gel purification kit (Qiagen). Eluted fragments were end-labeled using γ-$P^{32}$ ATP and $T_4$ poly nucleotide kinase. 500 pg of the labeled probe was incubated with 500 ng of purified MBP-SNOW1 fusion protein at RT for 30 min. For competition purified protein was incubated with 100 ng of unlabeled fragments for 30 min at RT prior to their incubation with the labeled probe. The DNA-protein complex was resolved on 5% polyacrylamide gel in 0.5×TBE and visualized by autoradiography.

Transient expression assays: Full-length snow1 and AtMyb79 cDNA were cloned in Sma I and Sal I sites of a plant expression vector 2×35S-MCS-Nos. The plasmid DNA of resultant effector plasmid and a CBF3 promoter-luc reporter were delivered into *Arabidopsis* leaves using particle bombardment (Ohta et al 2001).

In-vitro pull down assay: In-vitro pull-down assays were conducted to confirm the physical interaction of Snow1 and Ice1. Full-length snow1 cloned in pGEM-T easy and AtMyb79 (cloned in EcoR I and Xho I sites of pBCSK Stratagene) were used. Full-length Ice1 and ABI2 were cloned in EcoRI/SalI and NcoI/EcoRI sites of pCITE4a. 2 µg each of the linearized plasmid were in vitro transcribed using Megascript T7 RNA polymerase kit (Ambion). 10 µg of the purified transcript of snow1 and AtMyb79 were in vitro translated using Flexi Rabbit Reticulocyte system (Promega) in presence of $^{35}$S-methionine. S-tag-Ice1 and S-tag-ABI2 transcripts were translated in absence of $^{35}$S-methionine and their proteins were purified using S-tag purification kit (Novagen) as per the manufacturer's instructions. S-Tag Ice1 and S-tag ABI2 bound on the S-Tag slurry were used to pull down $^{35}$S-labeled proteins. In another experiment $^{35}$S-labeled S-tag Ice was produced and was used for pull-down using either GST-Snow1 or GST-Myb79 proteins. Pull-down assays were conducted as described (Haftler et al 2000).

Expression and localization of Snow1: For construction of the Snow1 promotor—GUS fusion, a 2.0 kb fragment upstream to the start codon of snow1 cDNA was PCR amplified using CCC AAGCTTATACCATATCAAATCTGAGAAAG (SEQ ID NO: 18) and CGC GGATCCATTTGTGATTGCTGATAAAAGAAG (SEQ ID NO: 19) primers from the Col WT genomic DNA and was cloned in HindIII and BamHI sites of pCAMBIA1391Z. The resultant plasmid was mobilized into GV3101 strain *Agrobacterium* and transformed in Col-O *Arabidopsis* plants by the floral vacuum infiltration (Bechtold and Pelletier, 1998). The transgenic plants were selected on MS containing 30 mg/L of Hygromycin. Transgenic seedlings were histochemically stained with 5-bromo-4-chloro-3-indolyl-β-D-glucuronide at 21 days old as described in Jefferson et al (1987) and were visualized using a Olympus FZX12 dissecting microscope. For construction of the GFP fusion full-length Snow1 cDNA was PCR-amplified using CCG GAATTCATGGGAAGAGCTCCATGCTGTGAG (SEQ ID NO: 20) and CGC GGATCCCTAGCCAATACATCGAACCAGAAG (SEQ ID NO: 21) primers and cloned in EcoRI and BamHI sites of pEGAD vector containing a bialophos acetyltransferase selectable marker gene (Cutler et al., 2000). The resultant plasmid was mobilized into *Agrobacterium* strain GV3101 and subsequently transformed in *Arabidopsis* plants (Col-0 ecotype) by the floral vacuum infiltration (Bechtold and Pelletier, 1998). For confocal microscopy, Snow1:GFP transgenic seedlings selected on MS agar medium supplemented with 50 mg/L phosphinothricin were mounted on glass slides, and images were visualized using a Zeiss 510 Meta confocal microscope with a 488-nm excitation laser and a 522/DF35 emission filter.

Construction of Transgenic plants: Full-length Snow1 was amplified using GC TCTAGAATGGGAAGAGCTCCATGCTGTGA (SEQ ID NO: 22) and GG GGTACCCTAGCCAATACATCGAACCAGA (SEQ ID NO: 23) and was cloned in XbaI/KpnI sites of pRT105 vector. The cassette containing the $^{35}$S promoter-Snow1-nos terminator was excised from the resultant plasmid and was cloned in PstI site of pCAMBIA 3300 vector. The final construct was mobilized into *Agrobacterium* strain GV3101. Transformation of *Arabidopsis* plants (CBF3-luc background) was performed by *Agrobacterium*-mediated in planta infiltration. *Agrobacterim* GV3101 with Snow1 overexpression vector was used to obtain the Snow1 overexpression lines in the CBF3-LUC background. The T1 transgenic plants were selected by spraying 30 mg/L basta 3 times with 3 day interval 2 weeks after germination. Seeds from each T1 plant (T2) were individually collected and used for further analysis.

Results

Snow1 Expression is Higher in Ice1 Mutant Plants

RNA blot analysis was conducted to analyze the effect of ice1 mutation on the levels of snow1 transcript. Consistent with the microarray data, more snow1 transcript was observed under conditions of cold stress in ice1 plants than the wild type plants (CBF3:luc). Increased snow1 transcript was observed at 1 hour, 3 hour and 6 hour of cold treatment. However at 12 hours of cold stress the snow1 expression in ice1 was lower then the wild type plants. The RNA blot analysis also indicates that snow1 expression is up-regulated in response to cold treatment. Wild type plants showed cold stress induction of Snow1 transcript after 1 hour of cold stress and its expression peaked at 6 hour. Snow1 transcript was also detectable under unstressed conditions.

Snow1 is Constitutively Expressed in all Parts of the Plant

To analyze the distribution of snow1 RNA gel blot analysis was performed using RNA extracted from the root, stem, flower and silique. Snow1 was found to be expressed in all organs of the *Arabidopsis* plant. Transgenic plants were made expressing Gus gene under the control of Snow1 promoter. T1 lines of transgenic *Arabidopsis* plants were analyzed for the Gus expression. Gus expression was detected in roots, leaves, stem and floral parts further confirming that Snow1 is constitutively and ubiquitously expressed.

Yeast Two-hybrid Interaction

To determine whether Snow1 interacts with Ice1, a yeast 2-hybrid system was employed. Different portions of Ice1 protein were used as bait and full-length Snow1 was used as prey to study their interaction. Snow1 preferentially interacted with the C-terminal portion of Ice1. The interaction of Snow1 and Ice1 was specific as only the prey plasmid or AtMyb79 prey plasmid failed to interact with Ice1. C-terminal portion of Ice1 was further narrowed down by deletions and used as bait to fine map the interacting domain with Snow1. It was observed that the region corresponding to 358-494 amino acids of Ice1 interacted specifically with Snow1. Apart from 2-hybrid interactions, the present inventors used protein pull-down assays to confirm the interaction between Ice1 and Snow1. GST-Snow1 was able to pull down 35 S-labeled Ice1. Similarly S-tagged Ice1 was able to pull-down 35 S-labeled Snow1. Their interaction was specific as neither GST-Myb79 nor S-tagged ABI2 were able to pull-down either Ice1 or Snow1 proteins respectively. These results suggest that Snow1 interacts with Ice1.

Snow1 Binds to MYB Recognition Sites in the CBF3 Promoter

EMSA was carried out to determine the binding of Snow1 with CBF promoters. Different portions of the CBF promoters were PCR amplified and used for EMSA. In the promoter region of CBF1 promoter the distribution of the putative Myb recognition sequences is as follows 0 in region −1000/−750, 1 each in regions −750/−500, −500/−300 and −150/+1 and two in −300/−150. Similarly in CBF2 promoter sequences there are no putative Myb recognition in region −1000/−750 and one each in regions −500/−270 and −270/−20. Four different regions of the CBF3 promoter were also used in EMSA with MBP-Snow1 fusion protein. All the fragments had two MYB recognition sequences except the third fragment in which such sequence was absent.

One major complex was observed in the fragments corresponding to the regions −750/−500 and −500/−300 of CBF1 promoter, whereas other regions of CBF1 promoter had no binding with Snow1. When CBF2 promoter fragments were used binding was observed with the fragments corresponding to the regions −1000/−750 and −500/−270, whereas no binding was observed with −270/−20 region of CBF2. Snow1 was able to bind to all the four fragments of the CBF3 promoter. These complexes were abolished by the addition of increasing amounts of cold competitors with the same sequences. These results indicate that Snow1 binds to the CBF promoters and the binding is possibly mediated by the Myb sequences.

Snow1 Regulates CBF3 Expression

Transient expression assays were carried out to determine whether Snow1 can activate CBF3 expression. An effector plasmid was constructed by cloning full-length Snow1 cDNA under the control of CaMV35 S promoter. When the CaMV35-Snow1 and a CBF3-responsive reporter gene, CBF3-LUC, were delivered into *Arabidopsis* leaves by particle bombardment, the luciferase activity increased nearly six fold relative to the control with or without reporter plasmid containing only the CBF3-luc (FIG. 4A). The increase in activity was more than when CaMV35-Ice1 was used as an effector. When CaMV35-Snow1 and CaMV35-Ice1 were co-bombarded there was little change in the CBF3 driven luciferase activity as compared to when only CaMV35-Snow1 alone was used as effector. These results suggest that Snow1 positively enhance the CBF3 expression.

Sub-cellular Localization of Snow1

To examine the subcellular localization of the Snow1 protein, full-length Snow1 cDNA was fused in-frame at the C-terminal of the green fluorescent protein (GFP) coding sequence. GFP-Snow1 fusion driven by CaMV $^{35}$S promoter was used to make transgenic plants. Confocal imaging of GFP fluorescence in T1 transgenic plants showed that the GFP-Snow1 fusion protein is present in the nucleus (FIG. 4B), thereby confirming that Snow1 is nuclear localized under unstressed conditions.

Transgenic Analysis

Snow1 overexpression construct was introduced into *Agrobacterium* GV3101. *Agrobacterium* harboring Snow1 overexpression vector was used for the flower-dipping transformation of the wild type (CBF3-LUC) plants. Snow1 overexpression lines (T1) were then selected by their capability to resist to basta. With T2 seeds, CBF3-LUC luminescence intensities in the Snow1 overexpression lines were analyzed in T2 seedlings. As in the wild type, no detectable luminescence was observed in Snow1 overexpression lines without cold treatment. After cold treatment, however, Snow1 overexpression lines showed the higher CBF3-LUC expression than the wild type. It should be noted that as the present inventors used Snow1 overexpression T2 lines (segregating population), the luminescence intensities of seedlings with higher luminescence in Snow1 overexpression T2 lines were used for the comparison with the wild type intensities. During the cold treatment the luminescence intensities remained higher in Snow1 overexpression lines than the wild type. Interestingly, one Snow1 overexpression line showed the lower luminescence intensities all the time tested suggesting the co-suppression of Snow1.

Numerous modifications and variations on the present invention are possible in light of the above teachings. It is, therefore, to be understood that within the scope of the accompanying claims, the invention may be practiced otherwise than as specifically described herein.

REFERENCES

Guy, C. L. 1990. Cold acclimation and freezing stress tolerance: Role of protein metabolism. *Annu. Rev. Plant Physiol. Plant Mol. Biol.* 41: 187-223.

Hughes, M. and Dunn, M. 1996. The molecular biology of plant acclimation to low temperature. *J. Exp. Bot.* 47: 291-305.

Browse, J. and Xin, Z. 2001. Temperature sensing and cold acclimation. *Curr. Opin. Plant Biol.* 4: 241-246.

Hsieh, T. H., Lee, J. T., Yang, P. T., Chiu, L. H., Charng, Y. Y., Wang, Y. C., and Chan, M. T. 2002. Heterology expression of the *Arabidopsis* C-repeat/dehydration response element binding factor 1 gene confers elevated tolerance to chilling and oxidative stresses in transgenic tomato. *Plant Physiol.* 129: 1086-1094.

Gong, Z., Lee, H., xiong, L., Jagendorf, A., Stevenson, B., and Zhu, J.-K. 2002. RNA helicase-like protein as an early regulator of transcription factors for plant chilling and freezing tolerance. *Proc. Natl. Acad. Sci.* 99: 11507-11512.

Thomashow, M. F. 1999. Plant cold acclimation, freezing tolerance genes and regulatory mechanisms. *Annu. Rev. Plant Physiol. Plant Mol. Biol.* 50: 571-599.

Tahtihaiju, S. and Palva, T. 2001. Antisense inhibition of protein phosphatase 2Caccelerates cold acclimation in *Arabidopsis thaliana*. *Plant J.* 26: 461-470.

Knight, H., Veale, E. L., Warren, G. J., and Knight, M. R. 1999. The sfr6 mutation in *Arabidopsis* suppresses low-temperature induction of genes dependent on the CRT/DRE sequence motif. *Plant Cell* 11: 875-886.

Mohapatra, S. S., Wolfraim, L., Poole, R. J., and Dhindsa, R. S. 1989. Molecular cloning and relationship to freezing tolerance of cold-acclimation-specific genes of alfalfa. *Plant Physiol.* 89: 375-380.

Yamaguchi-Shinozaki, K., and Shinozaki, K. 1994. A novel cisacting element in an *Arabidopsis* gene is involved in responsiveness to drought, low-temperature, or high-salt stress. *Plant Cell* 6: 251-264.

Stockinger, E. J. Gilmour, S. J., and Thomashow, M. F. 1997. *Arabidopsis thaliana* CBF1 encodes an AP2 domain-containing transcription activator that binds to the C-repeat/DRE, a cisacting DNA regulatory element that stimulates transcription in response to low temperature and water deficit. *Proc Natl. Acad. Sci.* 94: 1035-1040.

Liu, Q., Sakuma, Y., Abe, H., Kasuga, M., Miura, S., Yamaguchi-Shinozaki, K., and Shinozaki, K. 1998. Two transcription factors, DREB1 and DREB2, with an EREBP/AP2 DNA binding domain, separate two cellular signal transduction pathways in drought- and low temperature-responsive gene expression, respectively, in *Arabidopsis*. *Plant Cell* 10: 1391-1406.

Chinnusarny, V., Ohta, M., Kanrar, S., Lee, B.-h., Hong, X., Agarwal, M., and Zhu, J.-K. 2003. ICE1, a master regulator of cold induced transcriptome and freezing tolerance in *Arabidopsis*. *Genes & Dev.* 17:1043-1054.

Shinwari, Z. K., Nakashima, K., Miura, S., Kasuga, M., Seki, M., Yamaguchi-Shinozaki, K., and Shinozaki, K. 1998. An *Arabidopsis* gene family encoding DRE/CRT binding proteins involved in low-temperature-responsive gene expression. *Biochem. Biophys. Res. Commun.* 250: 161-170.

Spelt, C., Quattrocchio, F., Mol, J. N. M., and Koes, R. 2000. Anthocyanin1 of petunia encodes a basic-helix-loop-helix protein that directly activates transcription of structural anthocyanin genes. *Plant Cell* 12: 1619-1631.

Walker, A. R., Davison, P. A., Bolognesi-Winfield, A. C., James, C. M., Srinivasan, N., Blundell, T. L., Esch, J. J., Marks, M. D., and Gray, J. C. 1999. The TRANSPARENT TESTA GLABRA1 locus, which regulates trichome differentiation and anthocyanin biosynthesis in *Arabidopsis*, encodes a WD40-repeat protein. *Plant Cell* 11: 1337-1349.

Ohta, M., Matsui, K., Hiratsu, K., Shinshi, H., and Ohme-Takagi, M. 2001. Repression domains of class II ERF transcriptional repressors share an essential motif for active repression. *Plant Cell* 13: 1959-1968.

Grotewold E, Sainz M B, Tagliani L, Hernandez J M, Bowen B, Chandler V L. 2000. Identification of the residues in the Myb domain of maize $C_1$ that specify the interaction with the bHLH cofactor R. Proc Natl Acad Sci USA. 97(25): 13579-84.

Liu, J. and Zhu, J.-K. 1997. Proline accumulation and salt-stressinduced gene expression in a salt-hypersensitive mutant of *Arabidopsis*. *Plant Physiol.* 114: 591-596.

Halfter, U., Ishitani, M. and Zhu, J.-K. 2000. The *Arabidopsis* SOS2 protein kinase physically interacts with and is activated by the calcium-binding protein SOS3. Proc. Natl. Acad. Sci. USA. 97: 3735-3740.

Bechtold N, Pelletier G. 1998. In planta *Agrobacterium*-mediated transformation of adult *Arabidopsis thaliana* plants by vacuum infiltration. Methods Mol. Biol. 82:259-66.

Jefferson R A, Kavanagh T A, Bevan M W. 1987. GUS fusions: beta-glucuronidase as a sensitive and versatile gene fusion marker in higher plants. *EMBO J* 6(13): 3901-3907.

Cutler S R, Ehrhardt D W, Griffitts J S, Somerville C R. 2000. Random GFP::cDNA fusions enable visualization of subcellular structures in cells of *Arabidopsis* at a high frequency. Proc Natl Acad Sci USA. 97(7): 3718-23.

What we claim is:

1. An isolated polynucleotide, which encodes a protein consisting of the amino acid sequence of SEQ ID NO:2.

2. A vector comprising the isolated polynucleotide of claim 1.

3. A host cell comprising the isolated polynucleotide of claim 1.

4. A plant cell comprising the isolated polynucleotide of claim 1.

5. A transgenic plant comprising the isolated polynucleotide sequence of claim 1.

6. The transgenic plant of claim 5, wherein said plant is *Arabidopsis thaliania*.

7. The transgenic plant of claim 5, wherein said plant is selected from the group consisting of wheat, corn, peanut cotton, oat, and soybean plant.

8. The transgenic plant of claim 5, wherein the isolated polynucleotide is operably linked to an inducible promoter.

* * * * *

UNITED STATES PATENT AND TRADEMARK OFFICE
CERTIFICATE OF CORRECTION

PATENT NO.       : 7,378,573 B2                                        Page 1 of 1
APPLICATION NO.  : 10/958411
DATED            : May 27, 2008
INVENTOR(S)      : Zhu et al.

It is certified that error appears in the above-identified patent and that said Letters Patent is hereby corrected as shown below:

On the title page, Item (73), the Assignee's city is incorrect. Item (73) should read:

-- (73) Assignee:   Arizona Board of Regents on Behalf of University of Arizona,
        Tucson, AZ (US) --

Signed and Sealed this

Twenty-ninth Day of July, 2008

JON W. DUDAS
*Director of the United States Patent and Trademark Office*

SEQUENCE LISTING

```
<160> NUMBER OF SEQ ID NOS: 23

<210> SEQ ID NO 1
<211> LENGTH: 822
<212> TYPE: DNA
<213> ORGANISM: Artificial Sequence
<220> FEATURE:
<223> OTHER INFORMATION: Synthetic DNA
```

<400> SEQUENCE: 1

```
atgggaagag ctccatgctg tgagaagatg gggttgaaga gaggaccatg gacacctgaa      60
gaagatcaaa tcttggtctc ttttatcctc aaccatggac atagtaactg gcgagccctc     120
cctaagcaag ctggtctttt gagatgtgga aaaagctgta gacttaggtg gatgaactat     180
ttaaagcctg atattaaacg tggcaatttc accaaagaag aggaagatgc tatcatcagc     240
ttacaccaaa tacttggcaa tagatggtca gcgattgcag caaaactgcc tggaagaacc     300
gataacgaga tcaagaacgt atggcacact cacttgaaga gagactcga agattatcaa      360
ccagctaaac ctaagaccag caacaaaaag aagggtacta aaccaaaatc tgaatccgta     420
ataacgagct cgaacagtac tagaagcgaa tcggagctag cagattcatc aaaccccttct   480
ggagaaagct tattttcgac atcgccttcg acaagtgagg tttcttcgat gacactcata     540
agccacgacg gctatagcaa cgagattaat atggataaca accgggaga tatcagtact      600
atcgatcaag aatgtgtttc tttcgaaact tttggtgcgg atatcgatga aagcttctgg     660
aaagagacac tgtatagcca agatgaacac aactacgtat cgaatgacct agaagtcgct     720
ggtttagttg agatacaaca agagtttcaa aacttgggct ccgctaataa tgagatgatt    780
tttgacagtg agatggaact tctggttcga tgtattggct ag                       822
```

<210> SEQ ID NO 2
<211> LENGTH: 276
<212> TYPE: PRT
<213> ORGANISM: Artificial Sequence
<220> FEATURE:
<223> OTHER INFORMATION: Synthetic Peptide

<400> SEQUENCE: 2

```
Met Gly Arg Ala Pro Cys Cys Glu Lys Met Gly Leu Lys Arg Gly Pro
1               5                   10                  15

Trp Thr Pro Glu Glu Asp Gln Ile Leu Val Ser Phe Ile Leu Asn His
            20                  25                  30

Gly His Ser Asn Trp Arg Ala Leu Pro Lys Gln Ala Gly Leu Leu Arg
        35                  40                  45

Cys Gly Lys Ser Cys Arg Leu Arg Trp Met Asn Tyr Leu Lys Pro Asp
    50                  55                  60

Ile Lys Arg Gly Asn Phe Thr Lys Glu Glu Asp Ala Ile Ile Ser
65                  70                  75                  80

Leu His Gln Ile Leu Gly Asn Arg Trp Ser Ala Ile Ala Ala Lys Leu
                85                  90                  95

Pro Gly Arg Thr Asp Asn Glu Ile Lys Asn Val Trp His Thr His Leu
            100                 105                 110

Lys Lys Arg Leu Glu Asp Tyr Gln Pro Ala Lys Pro Lys Thr Ser Asn
        115                 120                 125

Lys Lys Lys Gly Thr Lys Pro Lys Ser Glu Ser Val Ile Thr Ser Ser
    130                 135                 140

Asn Ser Thr Arg Ser Glu Ser Glu Leu Ala Asp Ser Ser Asn Pro Ser
145                 150                 155                 160

Gly Glu Ser Leu Phe Ser Thr Ser Pro Ser Thr Ser Glu Val Ser Ser
                165                 170                 175

Met Thr Leu Ile Ser His Asp Gly Tyr Ser Asn Glu Ile Asn Met Asp
            180                 185                 190

Asn Lys Pro Gly Asp Ile Ser Thr Ile Asp Gln Glu Cys Val Ser Phe
        195                 200                 205
```

```
Glu Thr Phe Gly Ala Asp Ile Asp Glu Ser Phe Trp Lys Glu Thr Leu
    210                 215                 220

Tyr Ser Gln Asp Glu His Asn Tyr Val Ser Asn Asp Leu Glu Val Ala
225                 230                 235                 240

Gly Leu Val Glu Ile Gln Gln Glu Phe Gln Asn Leu Gly Ser Ala Asn
                245                 250                 255

Asn Glu Met Ile Phe Asp Ser Glu Met Glu Leu Leu Val Arg Cys Ile
            260                 265                 270

Gly Ile Cys Glu
        275

<210> SEQ ID NO 3
<211> LENGTH: 2021
<212> TYPE: DNA
<213> ORGANISM: Artificial Sequence
<220> FEATURE:
<223> OTHER INFORMATION: Synthetic DNA

<400> SEQUENCE: 3
atcaaaaaaa aagtttcaat ttttgaaagc tctgagaaat gaatctatca ttctctctct      60
ctatctctat cttccttttc agatttcgct tcttcaattc atgaaatcct cgtgattcta     120
ctttaatgct tctctttttt tacttttcca agtctctgaa tattcaaagt atatatcttt     180
tgttttcaaa cttttgcaga attgtcttca agcttccaaa tttcagttaa aggtctcaac     240
tttgcagaat tttcctctaa aggttcagac tttggggtaa aggtgtcaac tttggcgatg     300
ggtcttgacg gaaacaatgg tggaggggtt tggttaaacg gtggtggtgg agaaagggaa     360
gagaacgagg aaggttcatg gggaaggaat caagaagatg gttcttctca gtttaagcct     420
atgcttgaag gtgattggtt tagtagtaac caaccacatc cacaagatct tcagatgtta     480
cagaatcagc cagatttcag atactttggt ggttttcctt ttaaccctaa tgataatctt     540
cttcttcaac actctattga ttcttcttct tcttgttctc cttctcaagc ttttagtctt     600 gaccctctc agcaaaatca gttcttgtca actaacaaca caagggttg tcttctcaat     660 gttccttctt ctgcaaaccc ttttgataat gcttttgagt ttggctctga atctggtttt     720
cttaaccaaa tccatgctcc tatttcgatg gggtttggtt ctttgacaca attggggaac     780
agggatttga gttctgttcc tgatttcttg tctgctcggt cacttcttgc gccgaaaagc     840
aacaacaaca cacaatgtt gtgtggtggt ttcacagctc cgttggagtt ggaaggtttt     900
ggtagtcctg ctaatggtgg ttttgttggg aacagagcga aagttctgaa gcctttagag     960
gtgttagcat cgtctggtgc acagcctact ctgttccaga acgtgcagc tatgcgtcag    1020 agctctggaa gcaaaatggg aaattcggag agttcgggaa tgaggaggtt tagtgatgat    1080
ggagatatgg atgagactgg gattgaggtt tctgggttga actatgagtc tgatgagata    1140
aatgagagcg gtaaagcggc tgagagtgtt cagattggag aggaggaaa gggtaagaag    1200 aaaggtatgc ctgctaagaa tctgatggct gagaggagaa ggaggaagaa gcttaatgat    1260
aggctttata tgcttagatc agttgtcccc aagatcagca aaatggatag agcatcaata    1320
cttggagatg caattgatta tctgaaggaa cttctacaaa ggatcaatga tcttcacaat    1380
gaacttgagt caactcctcc tggatctttg cctccaactt catcaagctt ccatccgttg    1440
acacctacac cgcaaactct ttcttgtcgt gtcaaggaag agttgtgtcc ctcttcttta    1500
ccaagtccta aggccagca agctagagtt gaggttagat taagggaagg aagagcagtg    1560
aacattcata tgttctgtgg tcgtagaccg ggtctgttgc tcgctaccat gaaagctttg    1620
```

-continued

```
gataatcttg gattggatgt tcagcaagct gtgatcagct gttttaatgg gtttgccttg    1680
gatgttttcc gcgctgagca atgccaagaa ggacaagaga tactgcctga tcaaatcaaa    1740
gcagtgcttt tcgatacagc agggtatgct ggtatgatct gatctgatcc tgacttcgag    1800
tccattaagc atctgttgaa gcagagctag aagaactaag tccctttaaa tctgcaattt    1860
tcttctcaac tttttttctt atgtcataac ttcaatctaa gcatgtaatg caattgcaaa    1920
tgagagttgt tttaaaatta agcttttgag aacttgaggt tgttgttgtt ggatacataa    1980
cttcaacctt ttattagcaa tgttaacttc catttatgtc t                         2021
```

<210> SEQ ID NO 4
<211> LENGTH: 494
<212> TYPE: PRT
<213> ORGANISM: Artificial Sequence
<220> FEATURE:
<223> OTHER INFORMATION: Synthetic Peptide

<400> SEQUENCE: 4

```
Met Gly Leu Asp Gly Asn Asn Gly Gly Gly Val Trp Leu Asn Gly Gly
1               5                   10                  15

Gly Gly Glu Arg Glu Glu Asn Glu Glu Gly Ser Trp Gly Arg Asn Gln
            20                  25                  30

Glu Asp Gly Ser Ser Gln Phe Lys Pro Met Leu Glu Gly Asp Trp Phe
        35                  40                  45

Ser Ser Asn Gln Pro His Pro Gln Asp Leu Gln Met Leu Gln Asn Gln
    50                  55                  60

Pro Asp Phe Arg Tyr Phe Gly Gly Phe Pro Phe Asn Pro Asn Asp Asn
65                  70                  75                  80

Leu Leu Leu Gln His Ser Ile Asp Ser Ser Ser Cys Ser Pro Ser
                85                  90                  95

Gln Ala Phe Ser Leu Asp Pro Ser Gln Gln Asn Gln Phe Leu Ser Thr
            100                 105                 110

Asn Asn Asn Lys Gly Cys Leu Leu Asn Val Pro Ser Ser Ala Asn Pro
        115                 120                 125

Phe Asp Asn Ala Phe Glu Phe Gly Ser Glu Ser Gly Phe Leu Asn Gln
    130                 135                 140

Ile His Ala Pro Ile Ser Met Gly Phe Gly Ser Leu Thr Gln Leu Gly
145                 150                 155                 160

Asn Arg Asp Leu Ser Ser Val Pro Asp Phe Leu Ser Ala Arg Ser Leu
                165                 170                 175

Leu Ala Pro Glu Ser Asn Asn Asn Thr Met Leu Cys Gly Gly Phe
            180                 185                 190

Thr Ala Pro Leu Glu Leu Glu Gly Phe Gly Ser Pro Ala Asn Gly Gly
        195                 200                 205

Phe Val Gly Asn Arg Ala Lys Val Leu Lys Pro Leu Glu Val Leu Ala
    210                 215                 220

Ser Ser Gly Ala Gln Pro Thr Leu Phe Gln Lys Arg Ala Ala Met Arg
225                 230                 235                 240

Gln Ser Ser Gly Ser Lys Met Gly Asn Ser Glu Ser Ser Gly Met Arg
                245                 250                 255

Arg Phe Ser Asp Asp Gly Asp Met Asp Glu Thr Gly Ile Glu Val Ser
            260                 265                 270

Gly Leu Asn Tyr Glu Ser Asp Glu Ile Asn Glu Ser Gly Lys Ala Ala
        275                 280                 285

Glu Ser Val Gln Ile Gly Gly Gly Gly Lys Gly Lys Lys Lys Gly Met
```

-continued

```
            290                 295                 300

Pro Ala Lys Asn Leu Met Ala Glu Arg Arg Arg Lys Lys Leu Asn
305                 310                 315                 320

Asp Arg Leu Tyr Met Leu Arg Ser Val Val Pro Lys Ile Ser Lys Met
                325                 330                 335

Asp Arg Ala Ser Ile Leu Gly Asp Ala Ile Asp Tyr Leu Lys Glu Leu
                340                 345                 350

Leu Gln Arg Ile Asn Asp Leu His Asn Glu Leu Glu Ser Thr Pro Pro
            355                 360                 365

Gly Ser Leu Pro Pro Thr Ser Ser Ser Phe His Pro Leu Thr Pro Thr
370                 375                 380

Pro Gln Thr Leu Ser Cys Arg Val Lys Glu Glu Leu Cys Pro Ser Ser
385                 390                 395                 400

Leu Pro Ser Pro Lys Gly Gln Gln Ala Arg Val Glu Val Arg Leu Arg
                405                 410                 415

Glu Gly Arg Ala Val Asn Ile His Met Phe Cys Gly Arg Arg Pro Gly
                420                 425                 430

Leu Leu Leu Ala Thr Met Lys Ala Leu Asp Asn Leu Gly Leu Asp Val
            435                 440                 445

Gln Gln Ala Val Ile Ser Cys Phe Asn Gly Phe Ala Leu Asp Val Phe
450                 455                 460

Arg Ala Glu Gln Cys Gln Glu Gly Gln Glu Ile Leu Pro Asp Gln Ile
465                 470                 475                 480

Lys Ala Val Leu Phe Asp Thr Ala Gly Tyr Ala Gly Met Ile
                485                 490
```

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
gatgggaaga gctccatgct g                                             21

<210> SEQ ID NO 6
<211> LENGTH: 30
<212> TYPE: DNA
<213> ORGANISM: Artificial Sequence
<220> FEATURE:
<223> OTHER INFORMATION: Synthetic DNA

<400> SEQUENCE: 6
ccgctcgagc tagccaatac atcgaaccag                                    30

<210> SEQ ID NO 7
<211> LENGTH: 23
<212> TYPE: DNA
<213> ORGANISM: Artificial Sequence
<220> FEATURE:
<223> OTHER INFORMATION: Synthetic DNA

<400> SEQUENCE: 7
tgagactggg attgaggttt ctg                                           23

<210> SEQ ID NO 8
<211> LENGTH: 21
<212> TYPE: DNA
<213> ORGANISM: Artificial Sequence

```
<220> FEATURE:
<223> OTHER INFORMATION: Synthetic DNA

<400> SEQUENCE: 8
caagcttgcc tgcaggtcga c                                              21

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9
cgggatccat gggaagagct ccatgctgtg                                     30

<210> SEQ ID NO 10
<211> LENGTH: 33
<212> TYPE: DNA
<213> ORGANISM: Artificial Sequence
<220> FEATURE:
<223> OTHER INFORMATION: Synthetic DNA

<400> SEQUENCE: 10
cgggatccga atggtggaag aagtttggag aaa                                 33

<210> SEQ ID NO 11
<211> LENGTH: 33
<212> TYPE: DNA
<213> ORGANISM: Artificial Sequence
<220> FEATURE:
<223> OTHER INFORMATION: Synthetic DNA

<400> SEQUENCE: 11
ccgctcgagt taacaaaatg gaatcaccaa gtt                                 33

<210> SEQ ID NO 12
<211> LENGTH: 17
<212> TYPE: DNA
<213> ORGANISM: Artificial Sequence
<220> FEATURE:
<223> OTHER INFORMATION: Synthetic DNA

<400> SEQUENCE: 12
ggatccttaa cagccac                                                   17

<210> SEQ ID NO 13
<211> LENGTH: 17
<212> TYPE: DNA
<213> ORGANISM: Artificial Sequence
<220> FEATURE:
<223> OTHER INFORMATION: Synthetic DNA

<400> SEQUENCE: 13
ggtaacggtt accctac                                                   17

<210> SEQ ID NO 14
<211> LENGTH: 17
<212> TYPE: DNA
<213> ORGANISM: Artificial Sequence
<220> FEATURE:
<223> OTHER INFORMATION: Synthetic DNA

<400> SEQUENCE: 14
ggtaattcaa ccgtaaa                                                   17
```

<210> SEQ ID NO 15
<211> LENGTH: 17
<212> TYPE: DNA
<213> ORGANISM: Artificial Sequence
<220> FEATURE:
<223> OTHER INFORMATION: Synthetic DNA

<400> SEQUENCE: 15
ggccttctag ttaaatt                                                17

<210> SEQ ID NO 16
<211> LENGTH: 17
<212> TYPE: DNA
<213> ORGANISM: Artificial Sequence
<220> FEATURE:
<223> OTHER INFORMATION: Synthetic DNA

<400> SEQUENCE: 16
ggaattacaa ctgcatg                                                17

<210> SEQ ID NO 17
<211> LENGTH: 17
<212> TYPE: DNA
<213> ORGANISM: Artificial Sequence
<220> FEATURE:
<223> OTHER INFORMATION: Synthetic DNA

<400> SEQUENCE: 17
ggataattaa ctacttt                                                17

<210> SEQ ID NO 18
<211> LENGTH: 32
<212> TYPE: DNA
<213> ORGANISM: Artificial Sequence
<220> FEATURE:
<223> OTHER INFORMATION: Synthetic DNA

<400> SEQUENCE: 18
cccaagctta taccatatca aatctgagaa ag                               32

<210> SEQ ID NO 19
<211> LENGTH: 33
<212> TYPE: DNA
<213> ORGANISM: Artificial Sequence
<220> FEATURE:
<223> OTHER INFORMATION: Synthetic DNA

<400> SEQUENCE: 19
cgcggatcca tttgtgattg ctgataaaag aag                              33

<210> SEQ ID NO 20
<211> LENGTH: 33
<212> TYPE: DNA
<213> ORGANISM: Artificial Sequence
<220> FEATURE:
<223> OTHER INFORMATION: Synthetic DNA

<400> SEQUENCE: 20
ccggaattca tgggaagagc tccatgctgt gag                              33

<210> SEQ ID NO 21
<211> LENGTH: 33
<212> TYPE: DNA
<213> ORGANISM: Artificial Sequence
<220> FEATURE:
<223> OTHER INFORMATION: Synthetic DNA

```
<400> SEQUENCE: 21
cgcggatccc tagccaatac atcgaaccag aag                             33

<210> SEQ ID NO 22
<211> LENGTH: 31
<212> TYPE: DNA
<213> ORGANISM: Artificial Sequence
<220> FEATURE:
<223> OTHER INFORMATION: Synthetic DNA

<400> SEQUENCE: 22
gctctagaat gggaagagct ccatgctgtg a                               31

<210> SEQ ID NO 23
<211> LENGTH: 30
<212> TYPE: DNA
<213> ORGANISM: Artificial Sequence
<220> FEATURE:
<223> OTHER INFORMATION: Synthetic DNA

<400> SEQUENCE: 23
ggggtaccct agccaataca tcgaaccaga                                 30
```